US005801050A

United States Patent [19]
Uchida et al.

[11] Patent Number: 5,801,050
[45] Date of Patent: Sep. 1, 1998

[54] METHOD FOR PREPARING ALGAL DETRITUS

[75] Inventors: Motoharu Uchida; Katsuyuki Numaguchi, both of Yokohama, Japan

[73] Assignee: Director-General of National Research Institute of Fisheries Science, Japan

[21] Appl. No.: 610,824

[22] Filed: Mar. 7, 1996

[30] Foreign Application Priority Data

Mar. 9, 1995 [JP] Japan .................................. 7-078314
Jun. 12, 1995 [JP] Japan .................................. 7-169204

[51] Int. Cl.$^6$ ............................................ C12N 1/12
[52] U.S. Cl. .............................. 435/257.1; 435/252.1; 435/259
[58] Field of Search ........................... 435/41, 257.1, 435/252.1, 259

[56] References Cited

U.S. PATENT DOCUMENTS 4,226,210  10/1980  Lockwood et al. .

OTHER PUBLICATIONS

S.H. Bowen, "Digestion and Assimilation of Periphytic Detrital Aggregate by *Tilapia mossambica*", *Trans. of Am. Fisheries Society* 110:239–245 (1981).

E.A.S. Linley et al., "Estimates of Bacterial Growth Yields Based on Plant Detritus" *Bulletin of Marine Science* 35(3):409–425 (1984).

D.J.W. Moriarty, "Methodology for Determining Biomass and Productivity of Microorganisms in Detrital Food Webs" Proceedings of the Conference on Detrital Systems for Aquaculture, Bellagio, Como, Italy, Aug. 26–31, 1985.

D.E. Padgett et al., "A Technique for Distinguishing Between Bacterial and Non–Bacterial Respiration in Decomposing *Spartina alterniflora*", *Hydrobiologia* 122:113–119 (1985).

M. Rieper–Kirchner, "Macroalgal Decomposition: Laboratory Studies with Particular Regard to Microorganisms and Meiofauna" *Helgolander Meeresunters* 44:397–410 (1990).

K.R. Tenore, "Utilization of Aged Detritus Derived from Different Sources by the Polychaete *Capitella capitata*", *Marine Biology* 44:51–55 (1977).

J.Y. Yingst, "The Utilization of Organic Matter in Shallow Marine Sediments by an Epibenthic Deposit–Feeding Holothurian", *J. Exp. Mar. Biol. Ecol.* 23:55–69 (1976).

P. Baumann et al., "Genus Alteromonas Baumann, Baumann, Mandel and Allen 1972, 418.$^{AL}$", Berger's Manual of Systematic Bacteriology. vol. 1, Williams & Wilkins, pp. 343–352 (1984).

M. Uchida et al., "Isolation of Laminaria–Frond Decomposing Bacteria from Japanese Coastal Waters" *Nippon Suisan Gakkaishi* 59(11):1865–1871 (1993).

M. Uchida, "Enzyme Activities of Marine Bacteria Involved in Laminaria–Thallus Decomposition and the Resulting Sugar Release" *Marine Biology* 123:639–644 (1995).

*Primary Examiner*—Leon B. Lankford, Jr.
*Attorney, Agent, or Firm*—Testa, Hurwitz & Thibeault, LLP

[57] ABSTRACT

Algal detritus particles are prepared by contacting algae with marine bacteria capable of attaching to and decomposing the algae under conditions sufficient to induce decomposition of the structural components of the algal tissue, thereby forming detritus suitable for use as a primary feed for marine organisms. Marine bacteria which belong to the genus Alteromonas can be used. Algal detritus made according to the invention is useful as a primary feed for larvae of fry (young fish), crustaceans or mollusks.

11 Claims, 18 Drawing Sheets

METHOD FOR PREPARING ALGAL DETRITUS

BACKGROUND OF THE INVENTION

1. Field of the Invention

The present invention relates to a method for preparing detritus particles from macroalgae (seaweed) or other marine plants, such as seagrass, wherein said particles are suitable for use as feeds, for example in aquaculture, for raising detritus feeding organisms such as the larvae of fry (young fish), crustacea, or mollusks.

2. Description of the Prior Art

It is well known that algal fronds can be decomposed by microbial organisms, such as bacteria, etc., which are attached to the their surfaces. Decomposed fragments derived from living organisms in nature are known generically as "biological residue" or "detritus."

In nature, most marine resources decompose to become detritus, and are incorporated into the detritus food chain, thereby contributing to the marine ecology. Although the marine detritus food chain is less well known than the grazing food chain (represented generally by a prey-predator relationship), it plays an important role in biological production, as can be inferred from the fact that detritus-like substances are omnipresent in the digestive organs of many biological organisms.

Bacterial cells involved in decomposition frequently attach to the surface of the detritus. In such cases, the bacteria themselves may be beneficial nutrients. Mechanisms in which bacteria involved in decomposition are useful as feeds for biological organisms are referred to as "microbial loops." A microbial loop is intimately involved with the detritus food chain.

Few attempts have been made to utilize the detritus food chain positively for industrial applications. No practical example thereof is known. It is believed that in order to be considered a good feed, detritus should satisfy the following requirements:

1) the particle diameter thereof must be sufficiently small to be easily taken up by the target organism;

2) the hard cell walls of plants must be decomposed or removed so that the plant detritus may be digested and absorbed easily by the organism;

3) the material must be fresh with high nutritive value;

4) microbial agents which can serve as nutrients must be attached thereto; and 5) the detritus must be capable of being suspended homogeneously in seawater, and have excellent floating properties.

Algal fronds degrade slowly under natural conditions, therefore it has been difficult to obtain detritus which satisfies all of these requirements. Recently, research on the preparation of spheroplasts and protoplasts from algae has been carried out. However, such research was directed toward breeding algae by cell fusion using an enzyme. An object of the present invention is to provide a method for efficiently preparing detritus from algae satisfying the above requirements utilizing the capability of selected marine bacteria to attach to and decompose algae.

SUMMARY OF THE INVENTION

The present invention relates to methods for preparing spheroplast detritus particles from algae using bacteria which are capable of decomposing intercellular substances of the algae so that the algae can be separated substantially into single cells. The present invention further includes methods for preparing protoplasmic detritus particles from algae having hard cell walls using bacteria to decompose the hard cell walls of the algae. The present methods generally comprise contacting the algae, or other marine plants, such as seagrass, with bacteria capable of attaching to and/or decomposing the algae or other marine plants. Alternatively, the detritus particles may be formed by mechanical disruption of the algae.

Single cell detritus particles (hereinafter referred to as SCD) obtained by the present invention preferably have a diameter of about 2–10 µm (average about 6 µm), which is small enough so that the larvae of marine animals or fry (young fish) can prey on them. Typically, the larvae or fry which would be consuming the SCD of the present invention are those having a body length in the range of from about 100 µm to several mm. SCDs of the present invention have high floating capability due to their small size, which is preferable for feed use. As a result of the present methods, hard structural substances present in algae cells are degraded or removed, and the resultant feed exhibits good digestibility. Detritus particles produced according to the invention are particularly useful as feeds in aquaculture systems.

The present methods for making substantially naked cytoplasm by using the decomposing capability of bacteria for removing hard cell walls, as described herein, can be applied for preparing detritus feed from any type of algae and related multi-cellular biological organisms, and from single-cell biological organisms, such as a phytoplankton. In general, the application of bacterial metabolic decomposing action may result in the loss of some of the feed efficacy which the whole alga has in nature. However, in the present invention, decomposition is carefully controlled and is completed after a short time, thereby minimizing catabolic loss. In another embodiment of the present invention, physical means can be used in addition to bacterial means to accomplish the decomposition process, thereby further reducing catabolic loss associated with bacterial degradation.

Bacterial cells tend to be attached to the surface of the SCD at high densities. In some instances, single cell particles obtained as decomposition products can provide good nutrients even if bacteria does not attach thereto, and such SCDs are included in the present invention. However, SCDs having bacteria attached are preferred. The presence of bacteria on the SCDs confers certain benefits, such as, for example, a higher protein content, because the protein content of bacteria generally is higher than that of algae; and some bacteria produce vitamins and/or highly unsaturated fatty acids, which are beneficial for the growth of young fish, resulting in a better nutrient. In addition, the bacteria may have anti-microbial activity, thereby reducing the incidence of disease in the organism being fed. The presence of antimicrobial bacteria also permits bio-control of the fish culturing system.

In a preferred embodiment, the present invention provides a method for preparing algal detritus using bacteria belonging to the genus Pseudoalteromonas. In this embodiment of the present method, Pseudoalteromonas bacteria capable of attaching to and/or decomposing the structural components of algal tissue is contacted with the algae under conditions sufficient to induce the bacteria to decompose the algae into detritus suitable for a primary feed comprising particles having substantially uniform diameter.

In a preferred embodiment, algae belonging to the class Phaeophyceae or Chlorophyceae preferably is used as the starting material in the present invention. Laminaria, Eisenia, Ecklonica, Undaria and Sargassum are examples of types of Phaeophyceae which are useful. These algae can be decomposed by the above described marine bacteria to form particles suitable for use as a primary feed. *Ulva pertusa*, Monostroma, Enteromorpha, and Acetabuleria are examples of types of Chlorophyceae. The cell walls of these plants can be decomposed by the action of the above marine bacteria, resulting in formation of protoplasmic detritus suitable for use as a primary feed comprising particles having substantially the same diameter. Bacteria which are most preferred for accomplishing the present invention include *Pseudoalteromonas espejiana*, especially *Pseudoalteromonas espejiana* AR06 strain (Deposit number: FERM BP-5024; isolated by the inventors from coastal waters at Yokosuka-city, Kanagawa prefecture, Japan).

The proliferation of bacteria is faster and requires less use of resources such as light or heat compared with that of phytoplankton or zooplankton, which are used for feed at present. Thus, using the present method, detritus feed can be produced at low cost and with less labor. The present invention provides an avenue for utilizing undeveloped or underdeveloped marine resources, such as *Ulva pertusa*, into value-added products in the marine environment. The concept of making use of and/or recycling marine resources has the advantage of preserving the environment. The present invention therefore provides promising technology in the field of marine ecology.

(A) in the figure shows the case without bacterial inoculation, and (B) shows the case with inoculation of the AR06 strain of bacteria.

Figure 3:
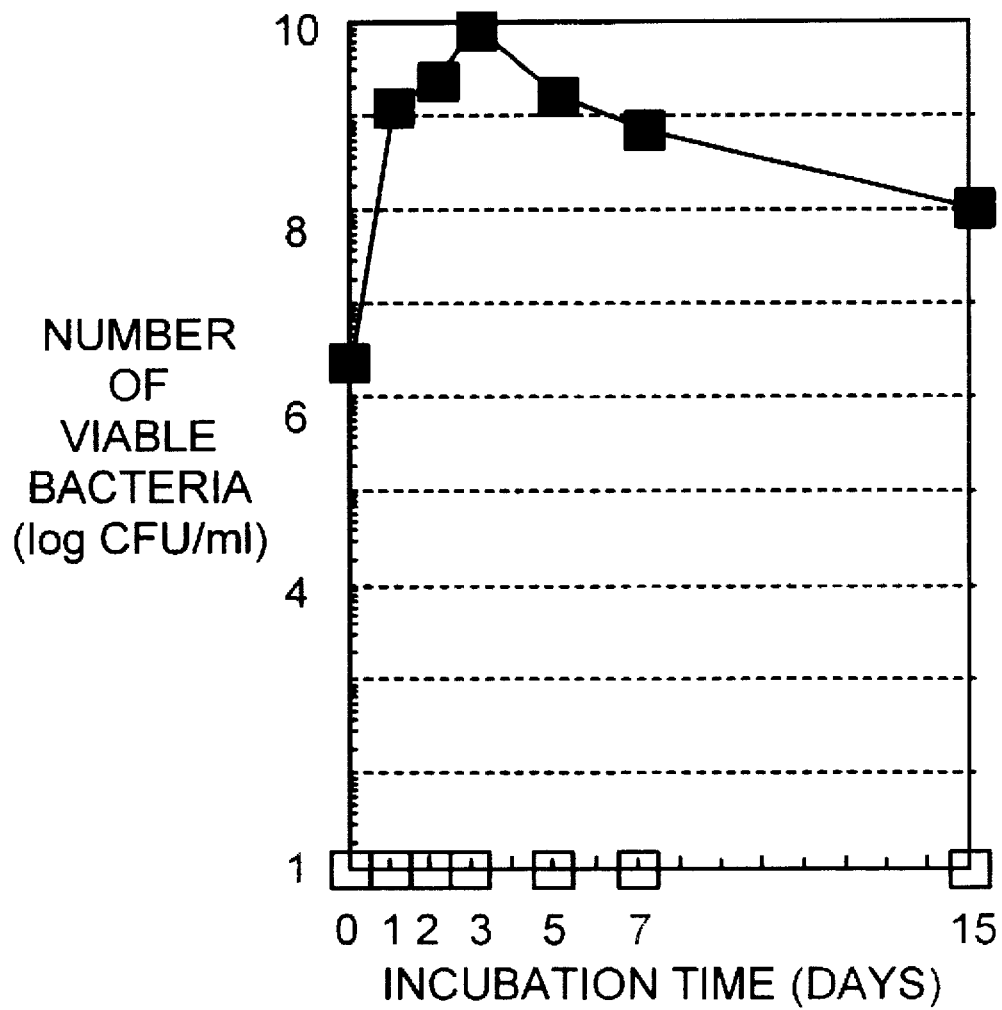

FIG. 3 shows a change in the viable count during Laminaria decomposition: ■ shows the results with inoculation, and □ shows the results without inoculation.

Figure 4:
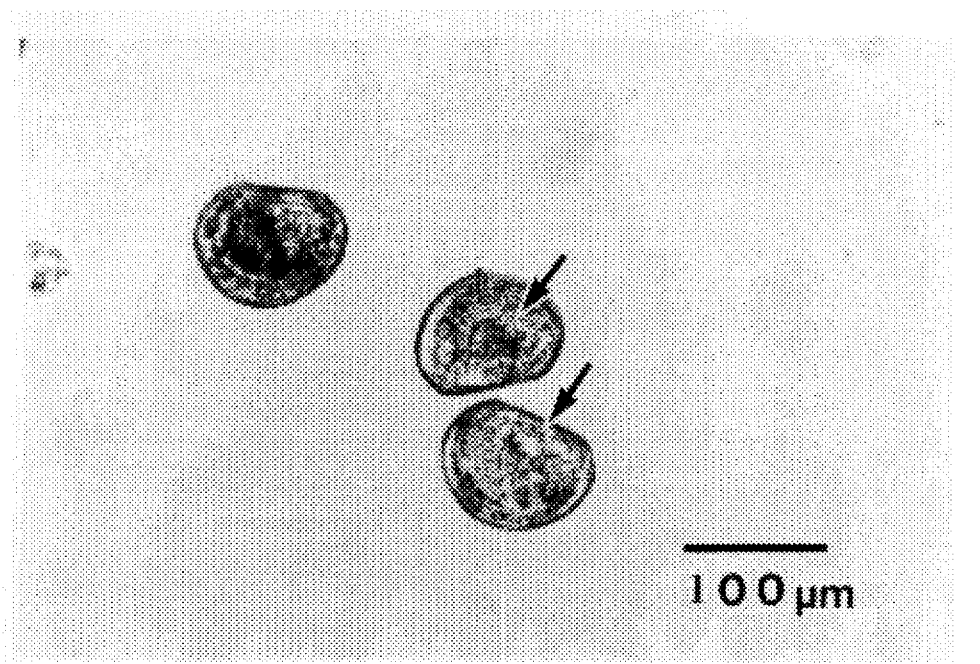

FIG. 4 is a microphotograph showing Laminaria SCD incorporated into the digestive organs of short-necked clam larvae.

Figure 5A:
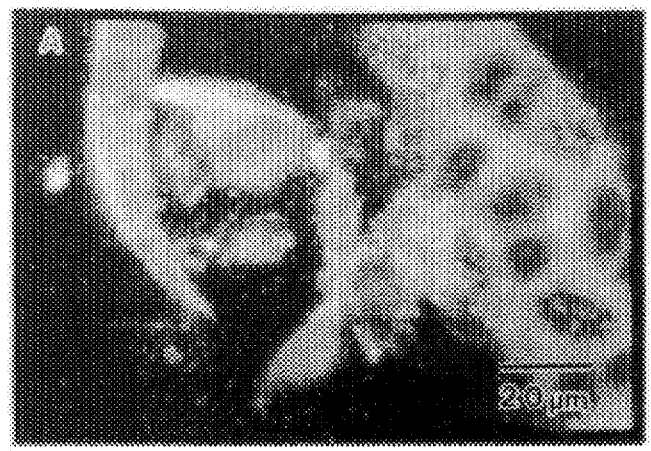

FIG. 5A is a microphotograph showing bacteria attached to the surface of and decomposing the cell walls of *Ulva pertusa*.

Figure 5B:
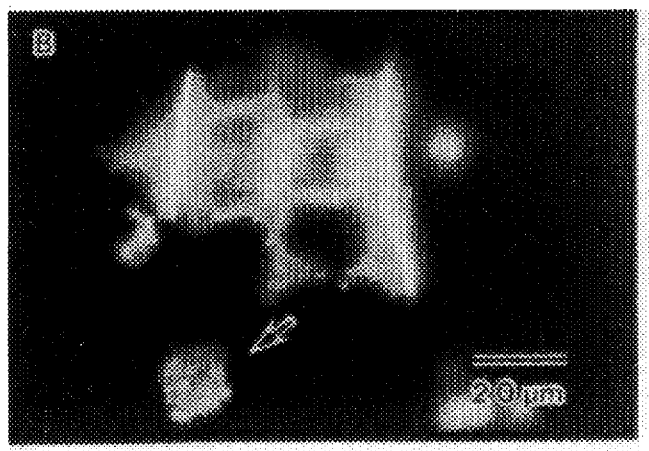

FIG. 5B is a microphotograph showing SCD released after degradation of the cell walls.

Figure 5C:
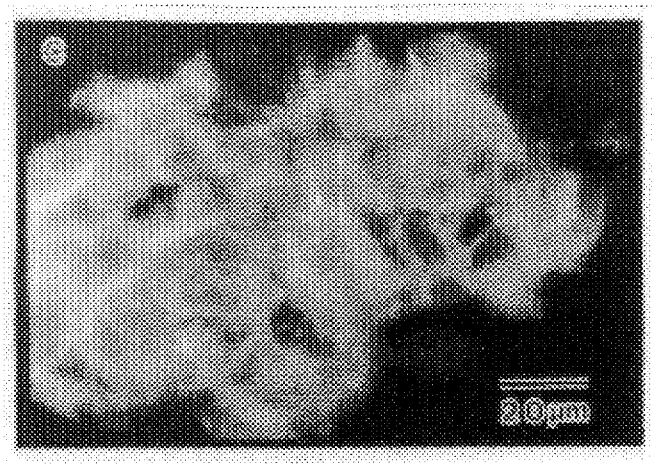

FIG. 5C is a microphotograph of a cast-off shell after SCD release.

Figure 5D:
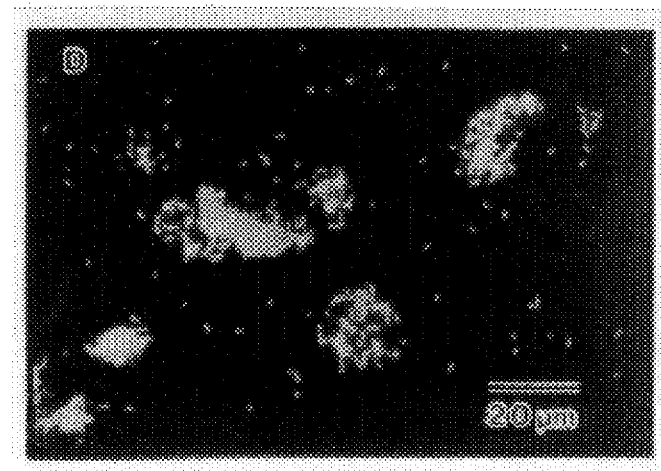

FIG. 5D is a microphotograph showing SCD with bacteria attached produced in seawater.

Figure 5E:
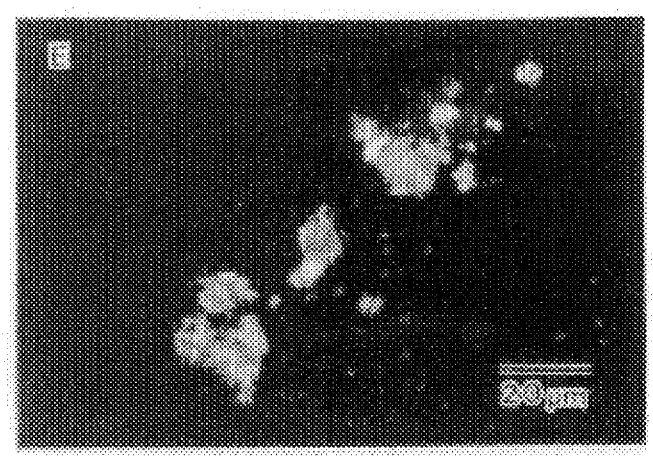

FIG. 5E is a microphotograph showing SCD becoming smaller as decomposition proceeds.

Figure 5F:
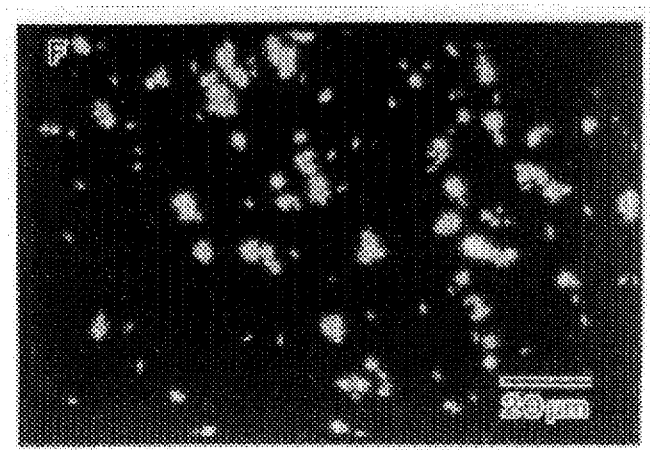

FIG. 5F is a microphotograph showing SCD becoming smaller as decomposition proceeds further.

Figure 6A:
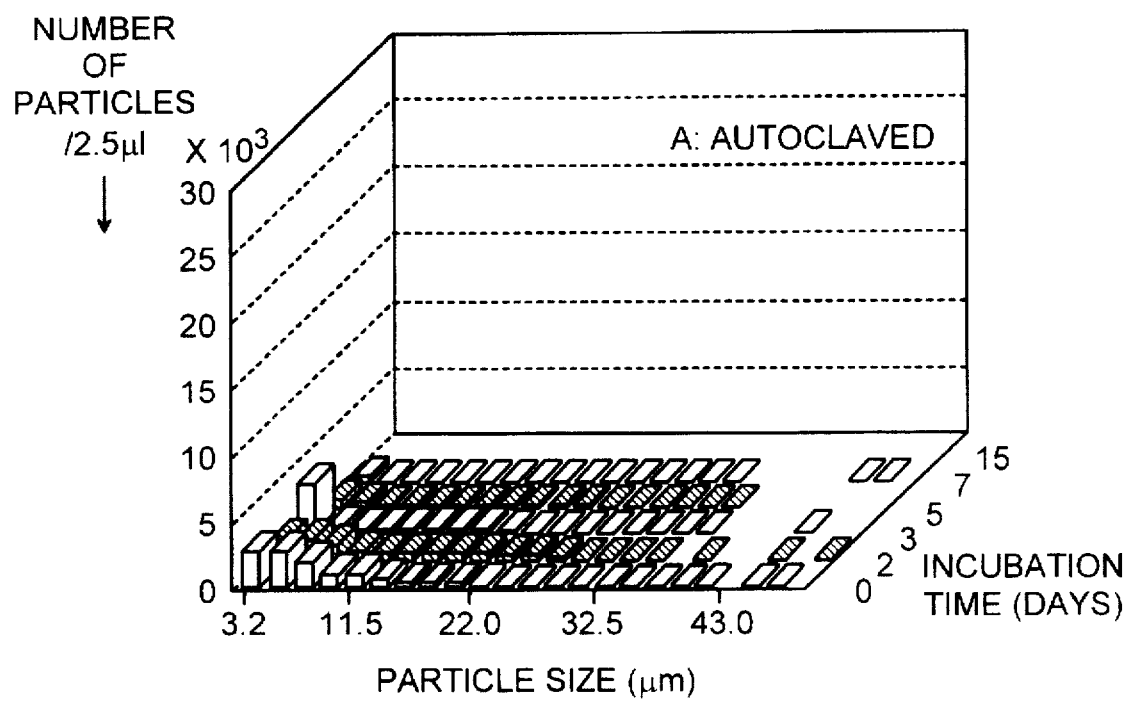
Figure 6B:
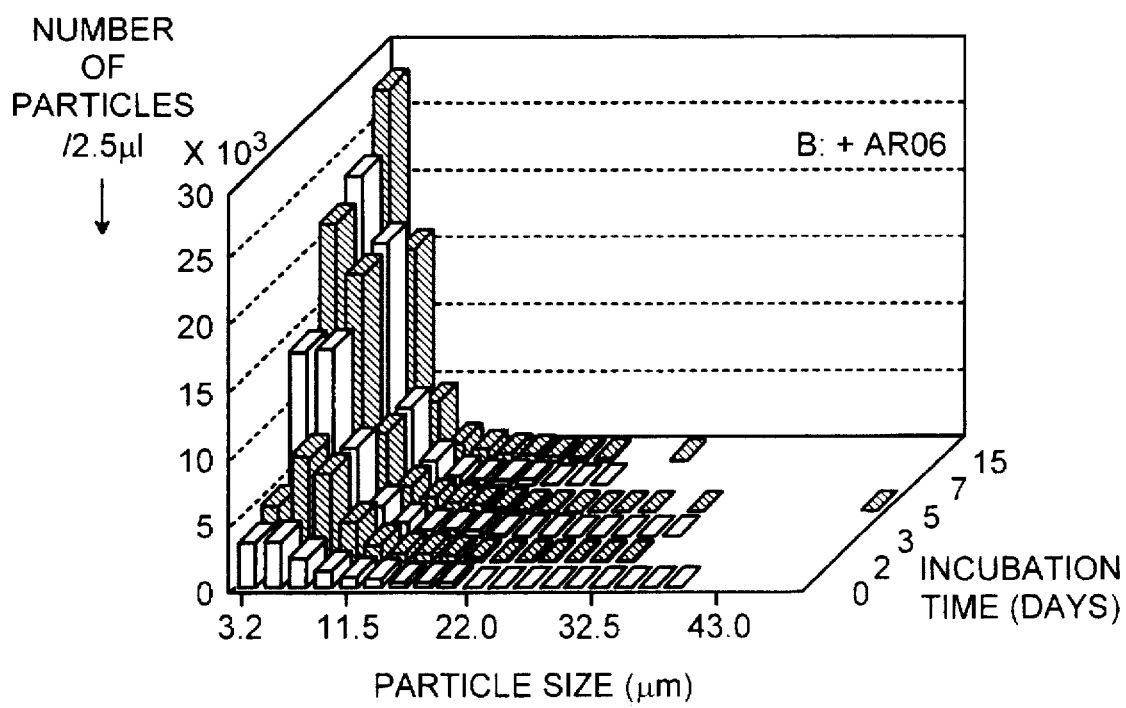

FIG. 6 shows a change in the diameter distribution of particles suspended in a culture during production of SCD:

(A) in the figure shows the results without bacterial inoculation, and (B) shows the results with inoculation of the AR06 strain.

Figure 7:
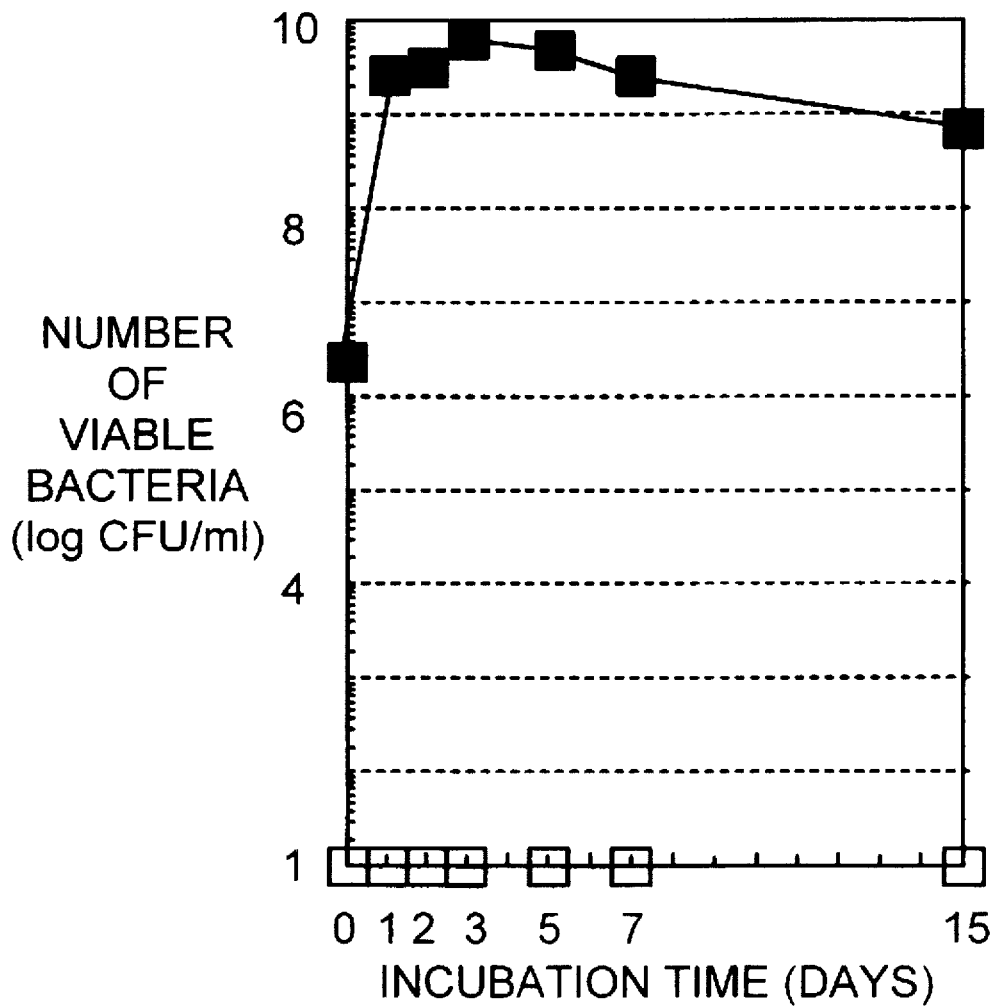

FIG. 7 shows viable bacteria decomposing *Ulva pertusa*: ■ shows an inoculated region, and □ shows the region without inoculation.

Figure 8:
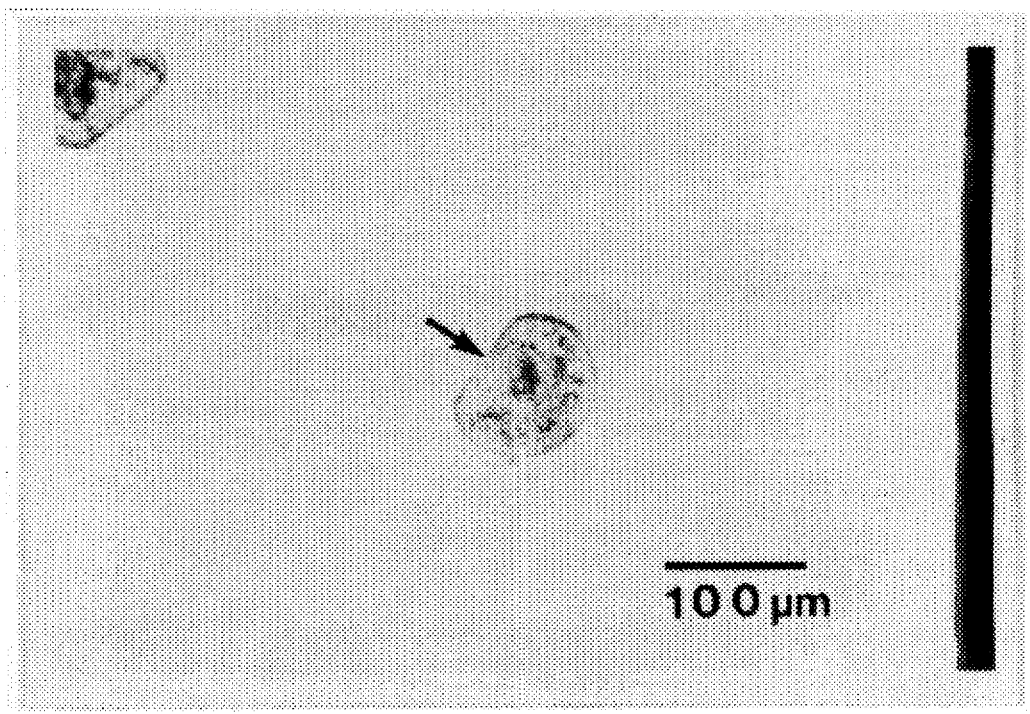
Figure 9A:
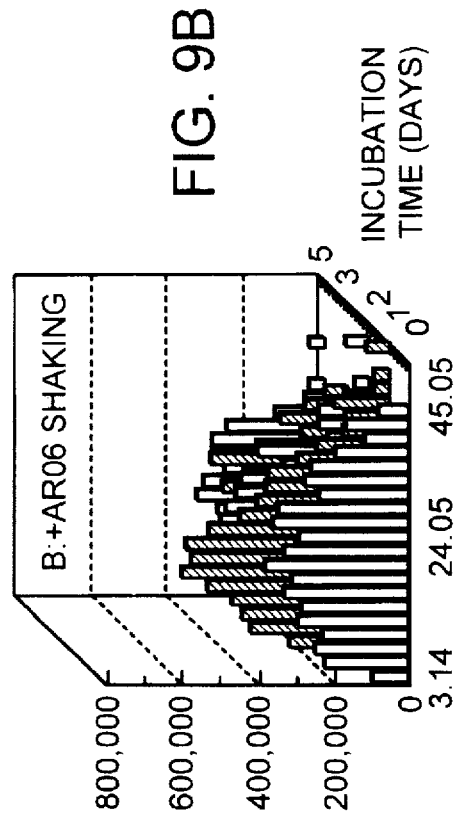
Figure 9B:
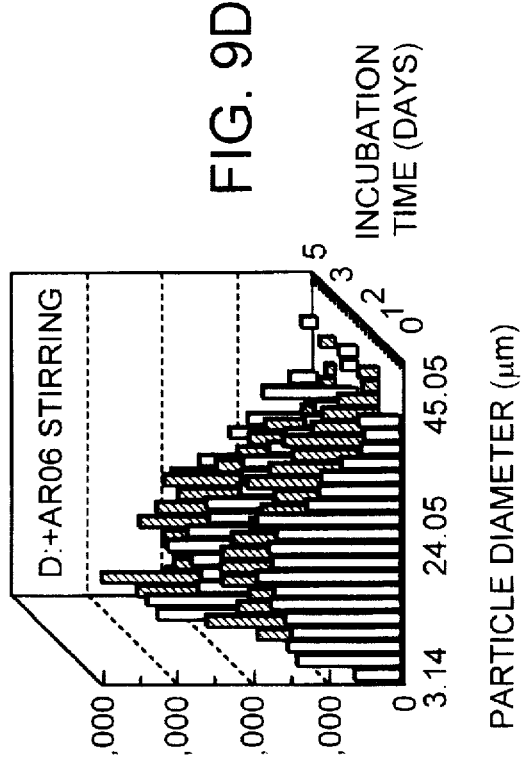
Figure 9C:
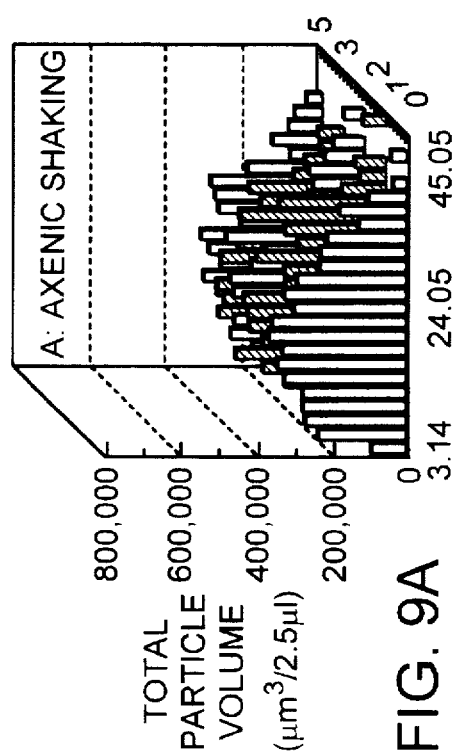
Figure 9D:
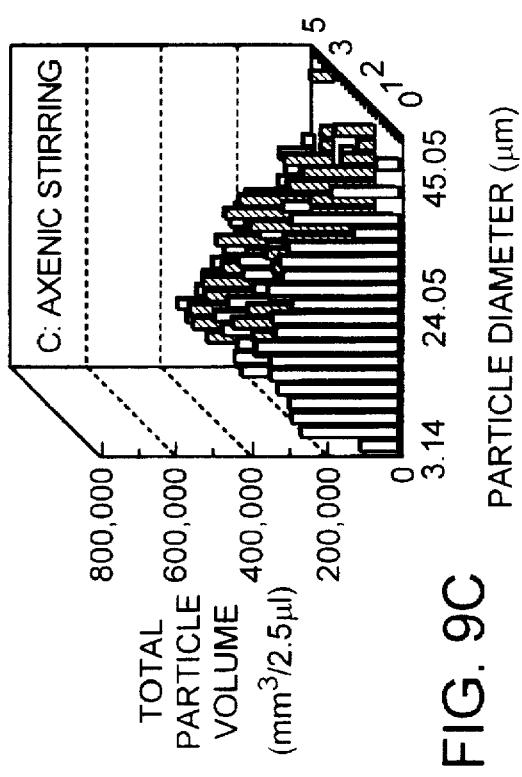

FIG. 8 is a microphotograph showing SCD of *Ulva pertusa* incorporated into the digestive organs of a short-necked clam.

FIG. 9 shows a comparison of the number of SCD produced from a Laminaria suspension using a shaken culture (a,b) with that of a stirred culture (c,d).

Figure 10:
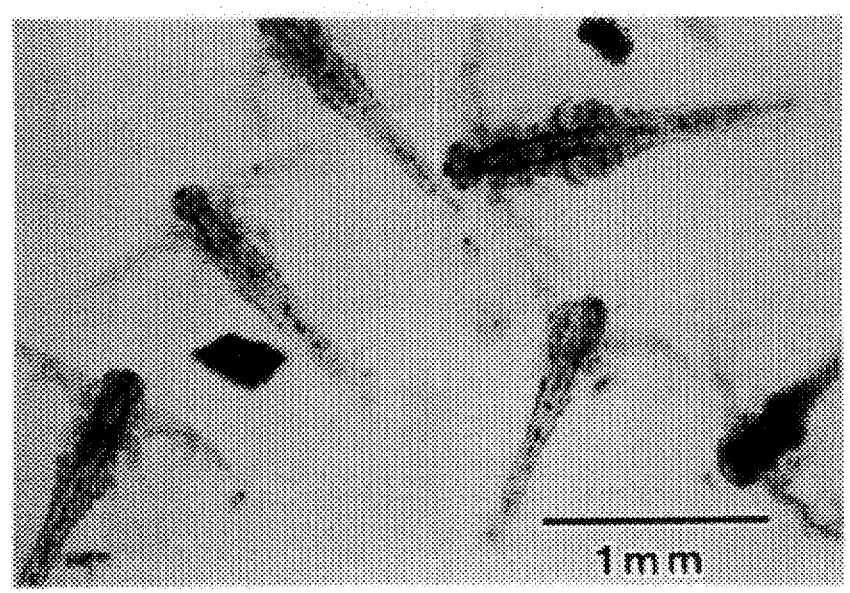

FIG. 10 is a microphotograph showing Artemia preying on Laminaria SCD particles.

Figure 11A:
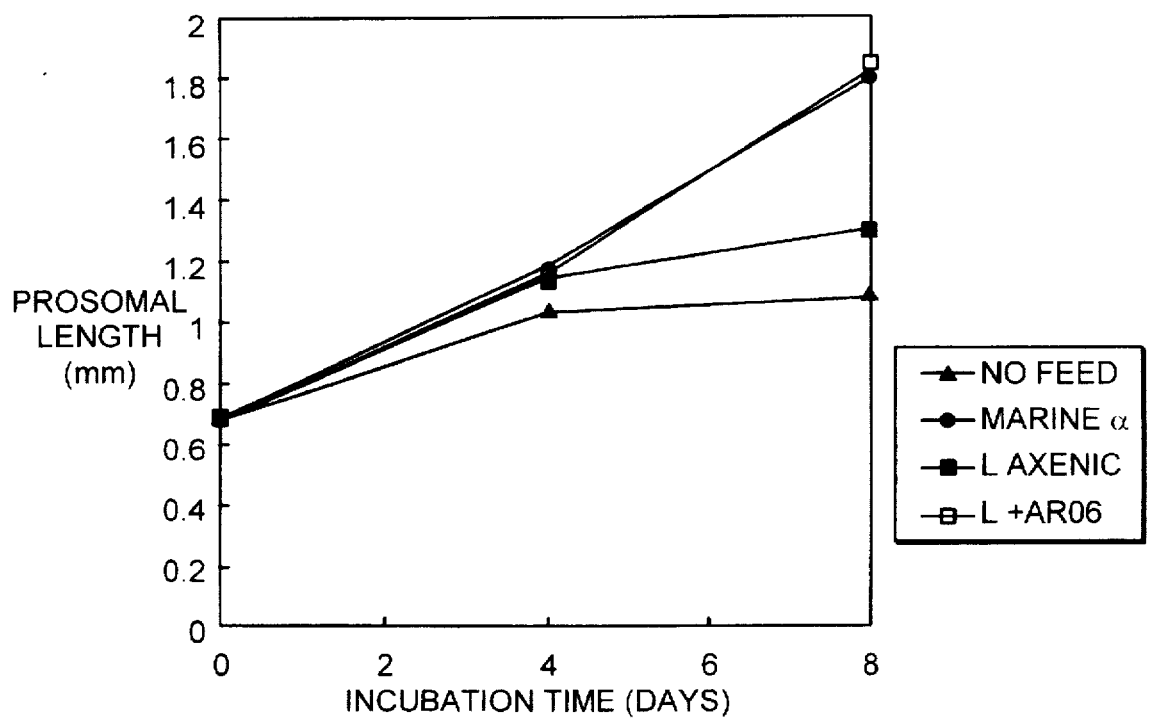

FIG. 11A shows the growth rate of Artemia.

Figure 11B:
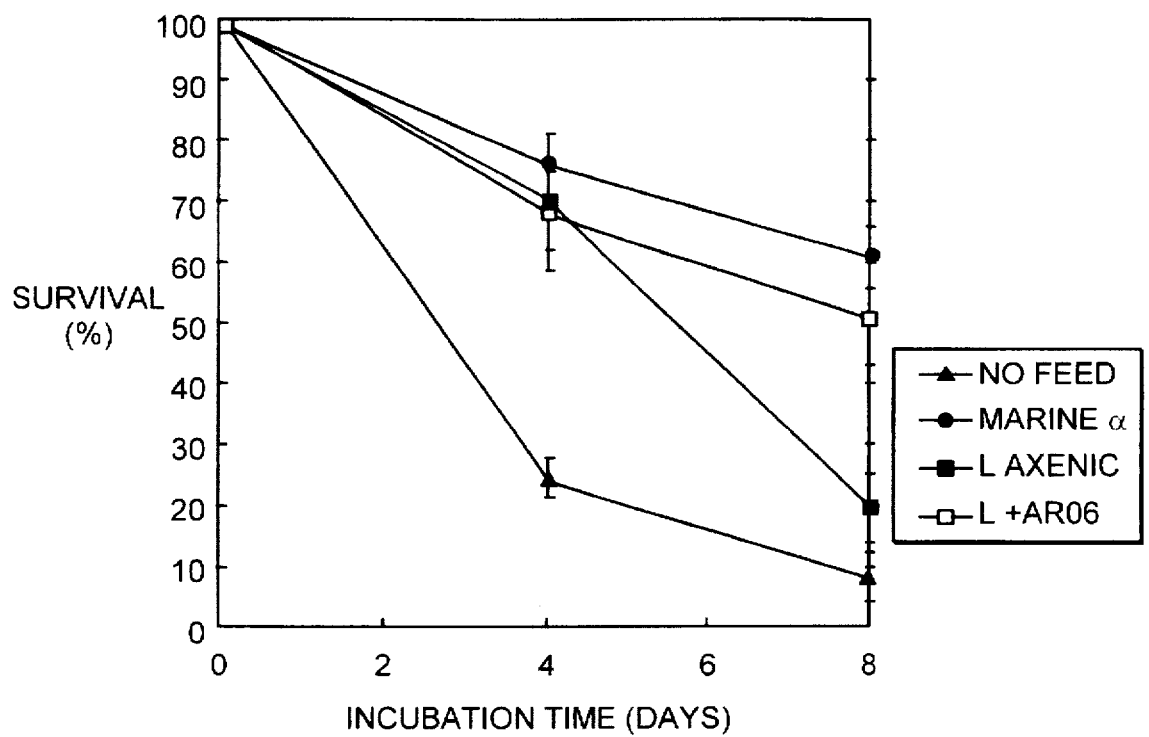

FIG. 11B shows the viable count of Artemia.

Figure 12:
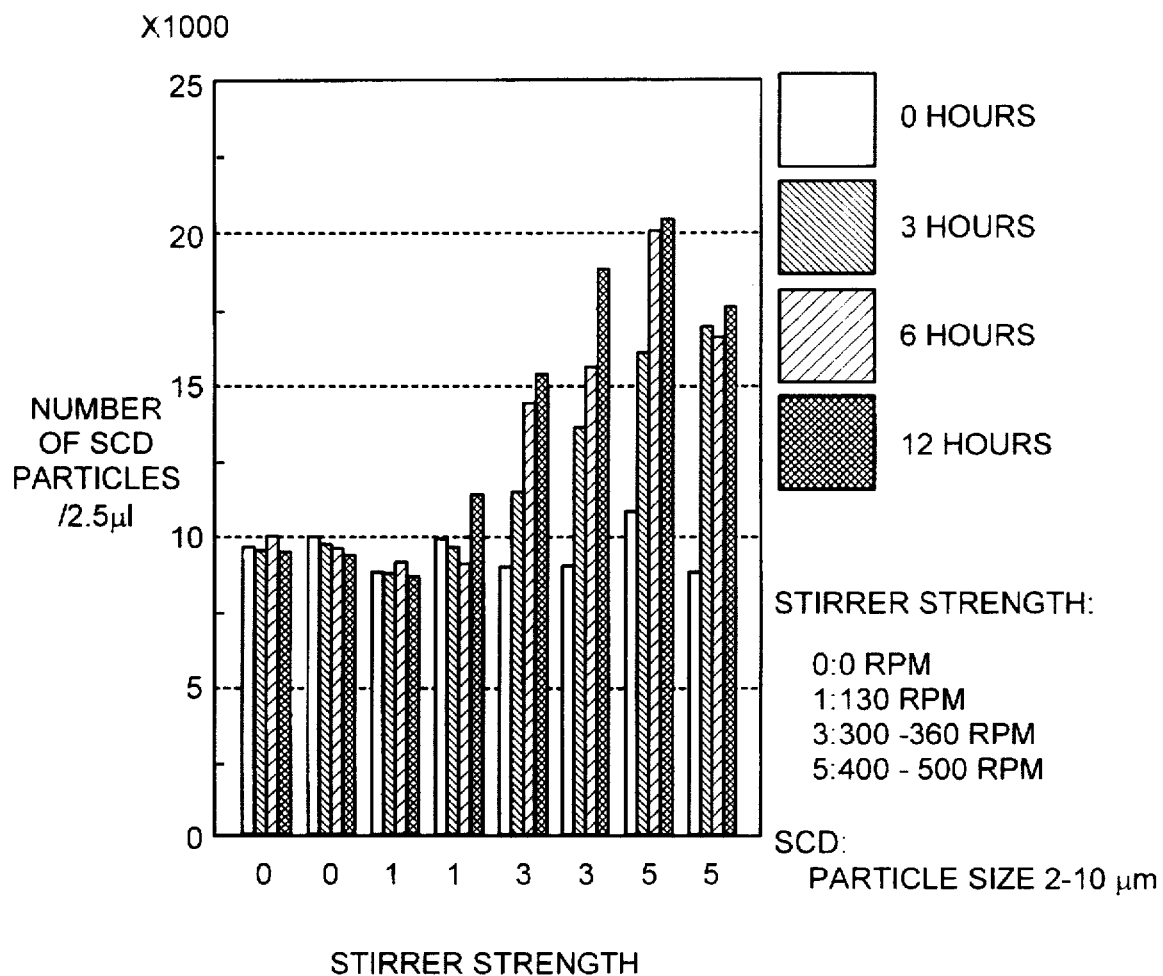

FIG. 12 shows the amount of SCD produced particles as the rate of stirring changed.

Figure 13A:
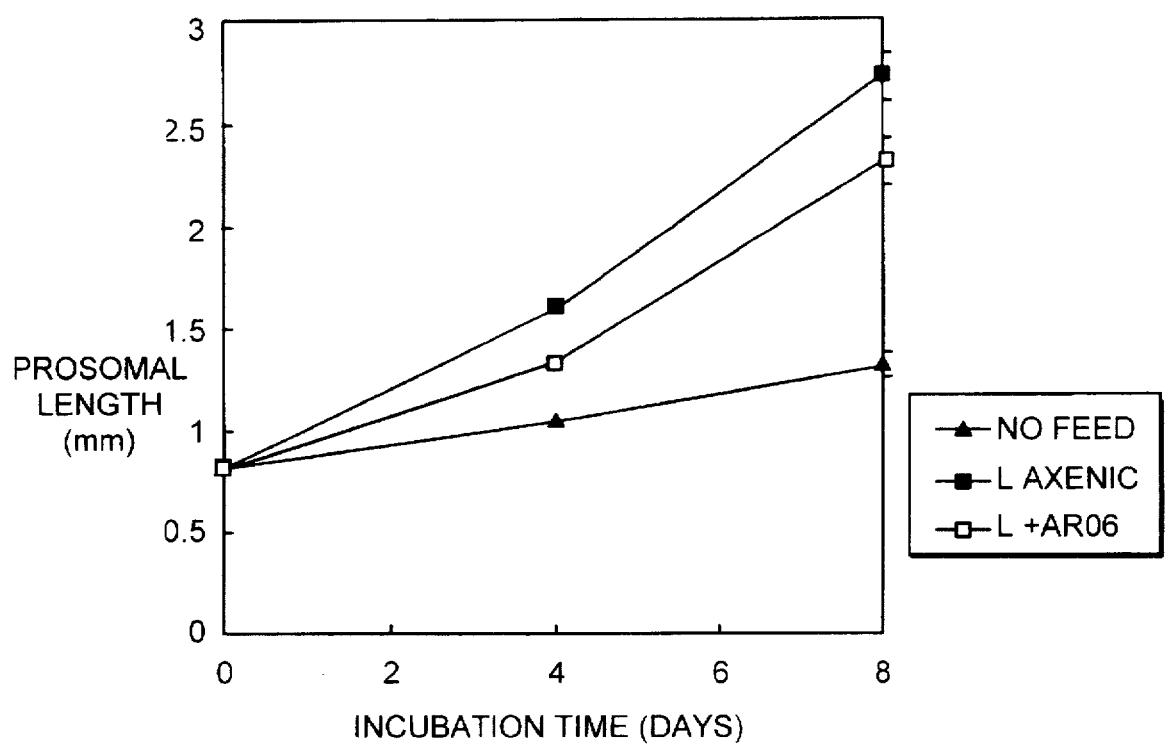

FIG. 13A shows the growth rate of Artemia.

Figure 13B:
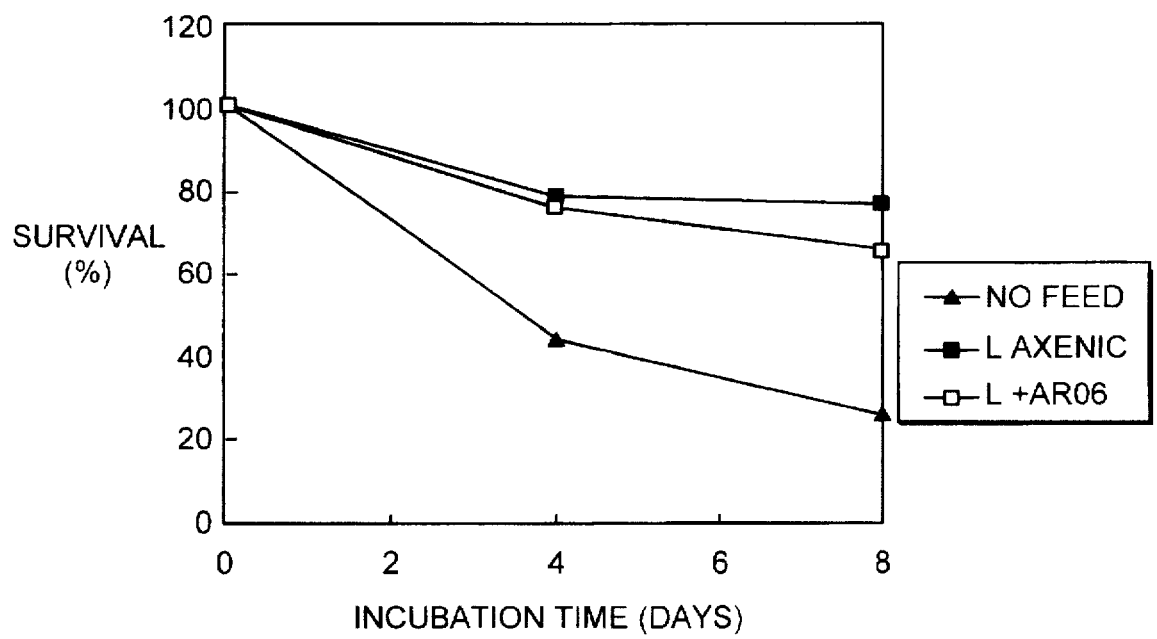

FIG. 13B shows the viable count of Artemia.

Figure 14:
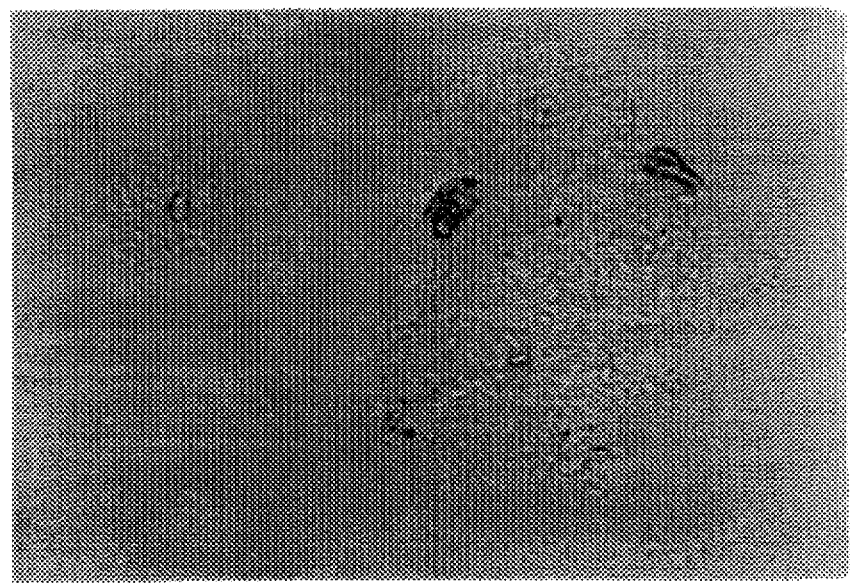

FIG. 14 is a microphotograph of Laminaria detritus particles with attached Pseudoalteromonas sp. strain T001 having no capability of making SCD which was purified using physical and microbiological decomposition.

DETAILED DESCRIPTION OF THE INVENTION

Bacterial cell lines useful in the present invention are characterized by the capability of decomposing at least one component, or multiple components, among the cellular structural polysaccharides of algae. These polysaccharides include, for example, those selected from the group consisting of aliginic acid, cellulose, agar-agar, fucoidin and carragaenan. The ability to produce detritus particles efficiently in large amounts and in a short time depends on the decomposing activity of the bacteria. It is important that the bacteria can attach to and proliferate on the surface of the algal tissue.

The inventors isolated a number of marine bacteria from seawater samples at more than ten locations in Japan, and investigated their bacterial properties, including their capability for decomposing algae and digesting various kinds of polysaccharides, and their ability to attach to and proliferate on algal surfaces. Bacteria belonging to the genus Psuedoalteromonas were found to be particularly useful for this purpose. More specifically, bacteria of the species *Psuedoalteromonas espejiana* are effective. A strain of *Psuedoalteromonas espejiana* designated AR06 having excellent properties with respect to the above objectives was identified and isolated as described below.

Samples of marine bacteria used in the present invention were obtained according to the following method which is described in detail by Uchida et. al. in *Nippon Suisan Gakkaishi*, 59(11); 1865–1871 (1993) which is hereby incorporated herein by reference.

Samples of seawater were taken separately at eleven locales off the coast of Japan, and ninety eight bacterial cell lines preying on Laminaria were isolated using seawater agar medium comprising 1 w/v % of damp-dried Laminaria powder (primary screening). The isolated bacterial cell lines were inoculated in a nutrient seawater medium comprising square pieces of Laminaria frond (1.5×3.0 cm), or in a seawater medium, and cultured by shaking at 20° C. for four weeks. The decomposition capability of the bacteria was assessed by determining the cutting strength of the Lamineria pieces taken out from the culture medium using a rheometer. Cell lines which decomposed Laminaria to a specific level of cutting strength were selected as Laminaria frond decomposing bacteria (second screening).

The enzymatic activity involved in decomposing various kinds of algal polysaccharides such as alginic acid, fucoidin, laminarin or cellulose, was determined in Laminaria decomposing bacteria obtained as described above using the produced amount of reducing saccharide as a parameter of decomposition. M. Uchida, *Marine Biology*, 123: 639–644 (1995). Bacterial cell lines having a decomposing activity higher than 10 units (1 unit=1 µg-glucose/hr/ml of reaction mixture) were selected as powerful Laminaria decomposing bacteria (third screening).

Bacterial cell lines selected as described above were inoculated into a seawater medium comprising 1 w %/v of damp-dried frond powder of Phaeophyceae (Laminaria) or Chlorophyceae (*Ulva pertusa*) and cultured by shaking to decompose the fronds. Microscopic observations were carried out during decomposition of the fronds to determine whether or not single cell detritus was produced, and whether or not bacteria attached to the surface of the produced detritus (fourth screening).

It was found that the marine bacteria isolated from the coastal waters at Arasaki of Yokosuka-city, Kanagawa-prefecture showed the most powerful activities. The characteristics of this bacteria are summarized in Table 1. According to the Burgey manual, this bacterial cell line was assigned to the genus and species *Psuedoalteromonas espejiana*. P. Baumann, M. J. Gauthier and L. Baumann: *Genus Alteromonas*, Baumann, Mandel and Allen 1972, 418, in Bergey's Manual of Systematic Bacteriology, volume 1, 343–352 (1984) Williams & Wilkins. This cell line was deposited with the National Institute of Bioscience and Human-Technology, Agency of Industrial Science & Technology, Ministry of International Trade & Industry, Japan and has a deposit number of FERM BP-5024 (hereinafter, this bacterial cell line will be referred to the AR06 strain).

TABLE 1

Bacteriological characteristics of the AR06 strain

| Characteristics | | Characteristics | |
|---|---|---|---|
| Cell shape | St rod | Production of: | |
| Gram reaction | − | Lipase | + |
| Spore | − | Gelatinase | + |
| Motility | + | Amylase | + |
| Flagellar arrangement | Polar | Alginase | + |
| Oxidase | + | Agarase | + |
| Catalase | + | Utilization of: | |
| OF | O | Glucose | + |
| Pigment | − | Mannose | + |
| Na requirement | + | Galactose | + |
| Growth in: | | Sucrose | + |
| 0% NaCl | − | Maltose | + |
| 1% NaCl | + | Cellobiose | − |
| Artificial seawater | + | Lactose | + |
| Growth at: | | Salicin | − |
| 4° C. | − | Gluconate | − |
| 35° C. | + | Citrate | + |

TABLE 1-continued

Bacteriological characteristics of the AR06 strain

| Characteristics | | Characteristics | |
|---|---|---|---|
| 40° C. | − | Glycerate | − |
| Reduction of $NO_3^-$ to $NO_2^-$ | − | L-Threonine | + |
| PHB accumulation | − | Putrescine | − |
| Quinone | Q-8 | | |
| GC content (Mol %) | 42 | | |

In the present invention, nutrient broth is not necessary to induce the bacteria to proliferate on and decompose the algae. A small amount of seed bacteria is sufficient to cause proliferation by preying on the algae in natural seawater. Accordingly, the detritus suspensions produced by the present methods do not contain excessive nutritional elements, such as nitrogen or phosphorus, which may cause eutrophication. As a result, detritus can be produced according to the present method with little pollution of the breeding water used in aquaculture.

Preparation of single cell algal detritus was achieved for the first time by the present invention. In a preferred embodiment, the AR06 strain is used to decompose the algae. However, even by using this strain the amount of SCD particles produced may not be sufficient when used with algae containing hard tissue, such as those belonging to the class Phaeophyceae. When algae containing hard tissue is used as the substrate, the yield of SCD can be improved by using a combination of physical means and bacterial decomposition. Such physical means may include, for example, shaking, stirring or sonication of the culture. Preparation of a large amount of SCD particles can be achieved in a short time by alternately shaking and stirring the culture, especially with a magnetic rotary stirrer. Any mechanical means can be used as the physical means of making SCD from algae, including, for example, stirring with a magnetic stirrer, shaking, or ultrasonication. In some instances, after the detritus particles are formed, bacterial activity still remains, and catabolic consumption of the formed SCD particles may proceed further, resulting in a decrease in the amount of SCD particles. In order to prevent this decrease, it is preferable to preserve the cultured mixture by stirring it at a cold temperature, for example, at about 2° C. Any temperature which slows or stops the bacterial activity can be applied.

Depending upon the feed requirements of the living organism to be bred, it may be preferable to alter the species of bacterium, and/or the genus of alga used. In some cases, bacteria capable of decomposing algae to make SCD may not be suitable for feed; or bacteria suitable for feed may not be able to make SCD. In these cases, combinations of bacterial strains may be used to achieve the desired result. All of the bacteria investigated for use in the present invention attached to the surface of algae. In another embodiment of the present invention, SCD can be produced from algae only by physical means, that is by stirring, shaking or otherwise manipulating the algae vigorously during the culture. In another embodiment, single cell detritus particles having attached bacteria with no ability to make SCD can be produced by adding bacteria having decomposing ability, or by using mechanical means to dispupt the algae. Thus, there is no limitation on selecting the species bacteria used, providing the strain or combination of strains used achieves the desired result.

Algae belonging to the classes Phaeophyceae, Chlorophyceae, Rhodophyceae, or any other algae, can be used in the present invention. Angiospermae is a type of seagrass which is distinguishable from seaweed. The structural polysaccharide of seagrass fronds is cellulose, thus, seagrasses belonging to this family also can be used. Types of Phaeophyceae include for example, Laminaria, Eisenia, Ecklonia, Undaria, *Sargassum fulvellum*, and Nemacytus. Types of Chlorophyceae include, for example, *Ulva pertusa*, Monostroma, Enteromorpha, or Acetabulaia. Types of Rhodophyceae include, for example, Gelidum, Gracilaria, Gloiopeltis, or Chondrus. Types of Angiospermae, include for example Zostera or Phyllospadix.

In breeding experiments using Artemia, as demonstrated in the exzmples set out below, it was found that Laminaria detritus prepared according to the present method was an excellent feed compared to a suspension of untreated Laminaria.

The present invention will be further illustrated by the following examples, which are not intended to be limiting in any way.

EXAMPLES

Example 1

Algal powder having a particle diameter less than 33 μm and an average particle diameter of 23 μm was obtained by milling and sieving damp-dried fronds of *Laminaria japonica* belonging to the class Phaeophyceae, the algae (0.5 g) was suspended in an Erlenmeyer flask containing 50 ml of aged sea water (90% concentration), and sterilized in an autoclave. Marine bacteria AR06 strain ($10^8$ cells) FERM BP 5024) were inoculated into the suspension of algae and cultured at 20° C. on a reciprocal shaker (120 rpm). Samples were periodically taken, and tissue changes were followed by microscopic observation, if necessary, after DAPI staining or safranine staining. Changes in the diameter distribution of algal particles were followed using a Coulter multisizer (Coulter Co., Ltd.).

Figure 1A:
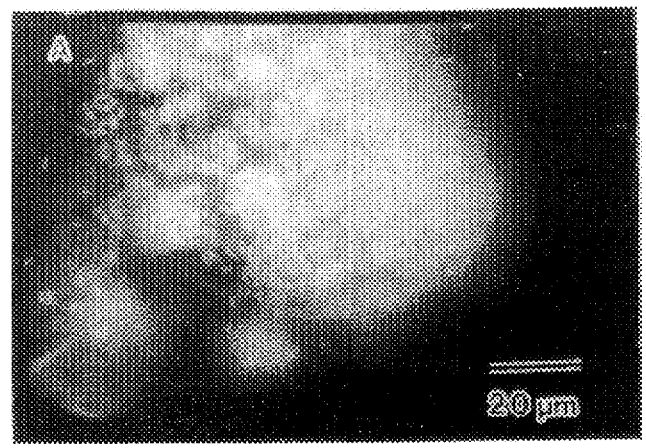
FIG. 1A is a microphotograph showing bacteria attached to the surface of and decomposing Laminaria algae.
Figure 1B:
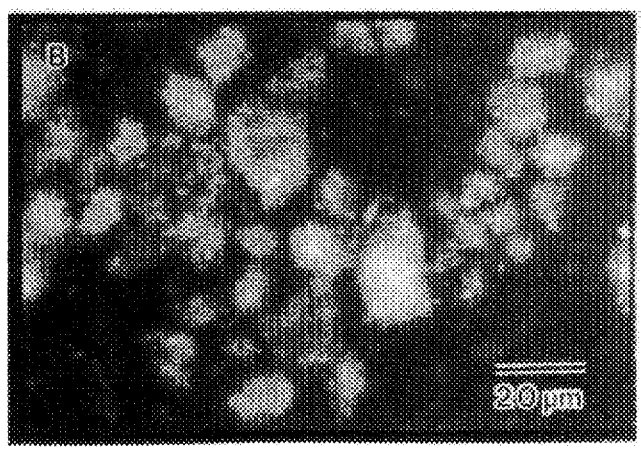
FIG. 1B is a microphotograph showing Laminaria particles decomposed into single cells by bacterial decomposition.
Figure 1C:
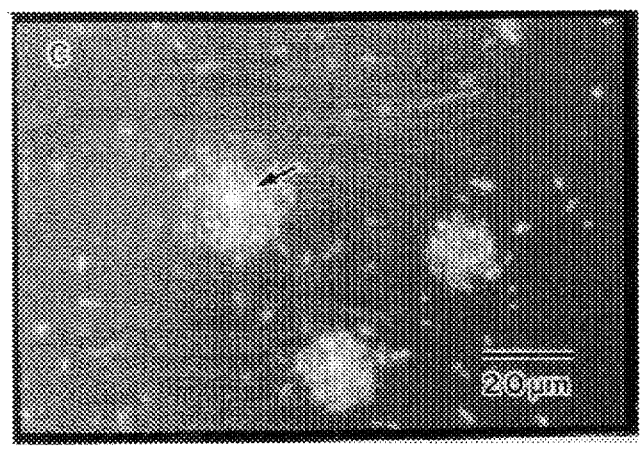
FIG. 1C is a microphotograph showing bacteria accumulated around SCD (single cell detritus) cytoplasm.
Figure 1D:
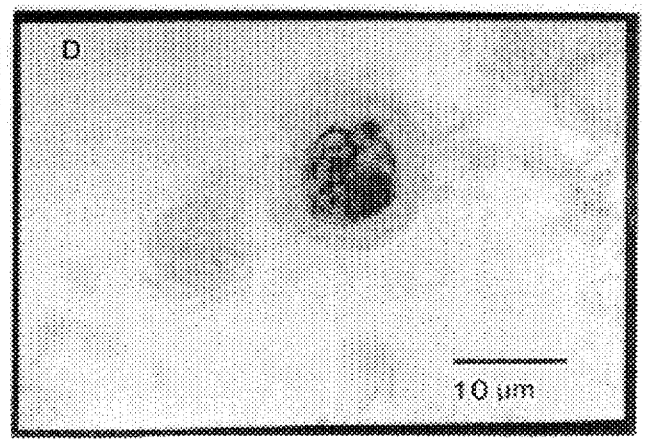
FIG. 1D is a microphotograph showing SCD including cytoplasm, and SCD losing cytoplasm just after separation.
Figure 1E:
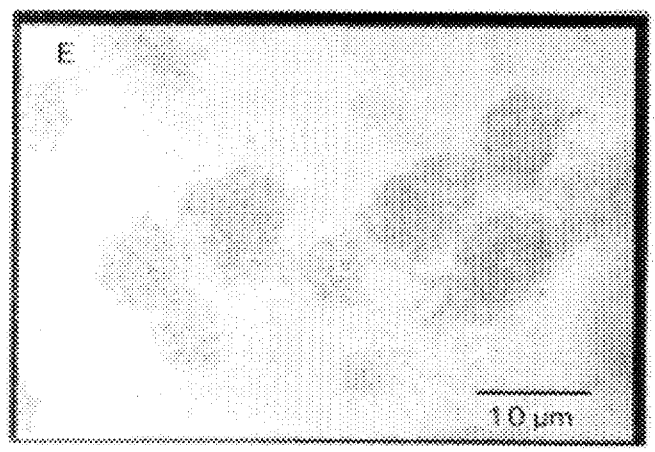
FIG. 1E is a microphotograph showing SCD losing cytoplasm produced in seawater.
Figure 2A:
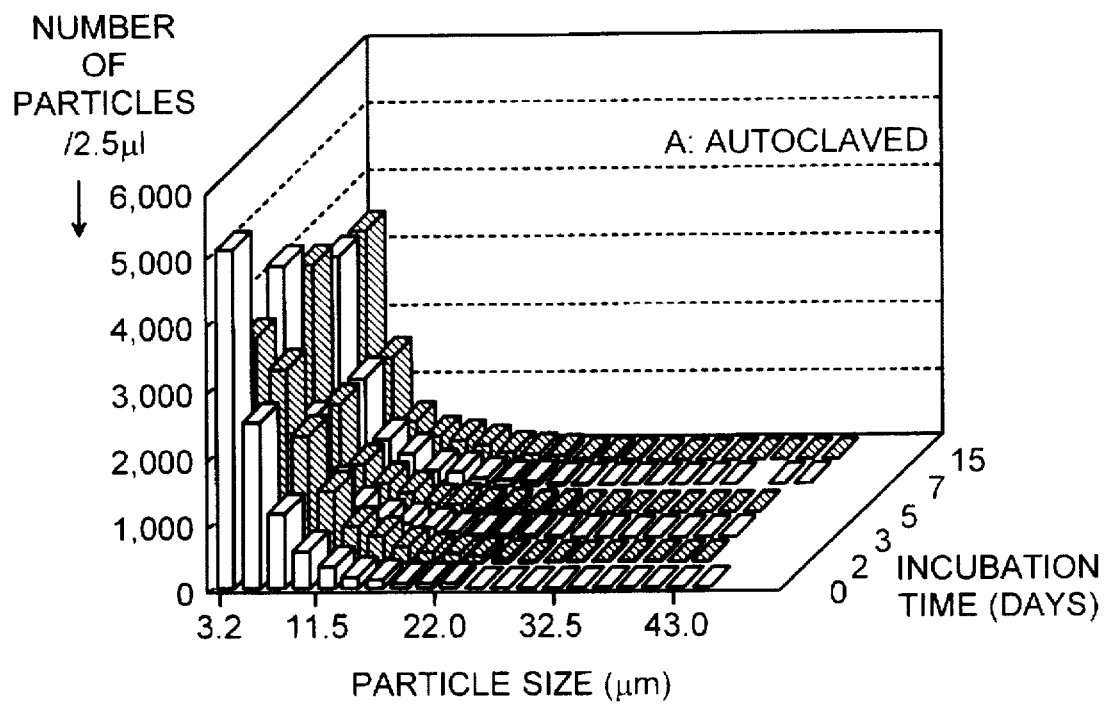
FIG. 2 shows a change in the diameter distribution of suspended particles in a culture during production of SCD.
Figure 2B:
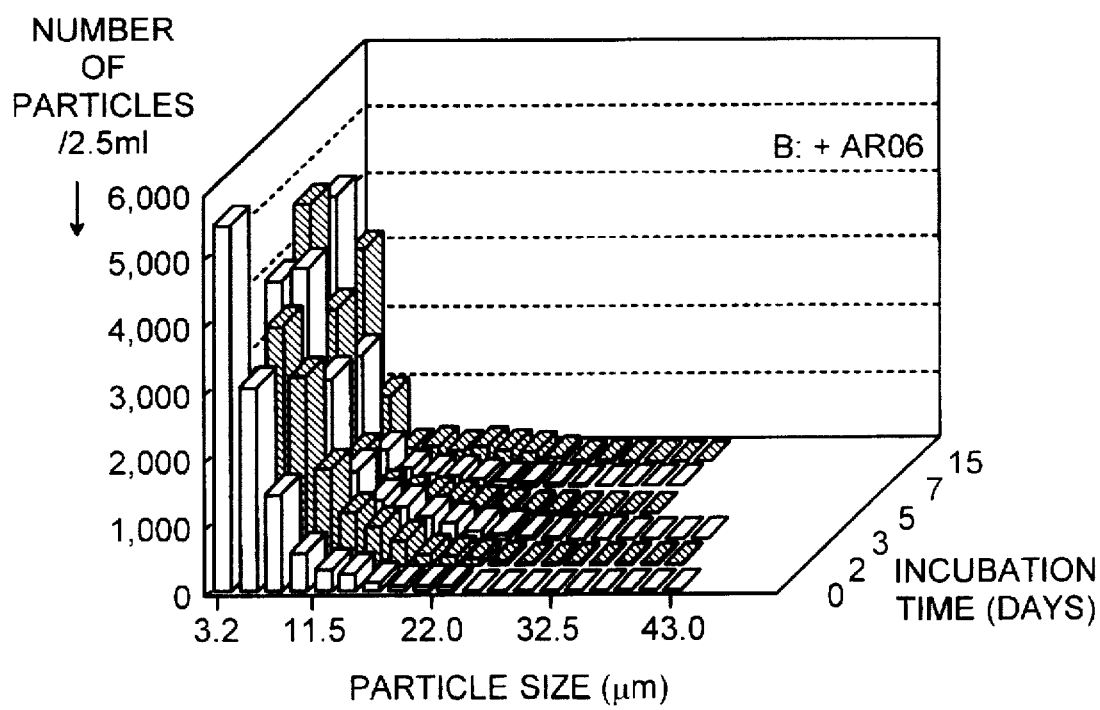

Results of the above experiment showed that bacterial adhesion and proliferation on the surface of the algal particles occurred within 24 hours of initiation of the culture. As shown in FIG. 1A, a number of bacterial cells attached to the surface of the algae. As decomposition proceeded further, it was observed that algal single cells could be dispersed by applying slight physical stimulation. FIG. 1B is a microphotograph showing that algae in the form of multicellular particles at an early stage became dispersed by pushing a sample under a cover glass slightly. Thus, SCD dispersed into single cells was obtained. FIG. 1C shows clearly that SCD is a dense aggregate of bacterial cells gathered around a core of cytoplasm. FIG. 1D is a microphotograph taken on separation from the algae and shows a number of particles comprising cytoplasmic components at an early stage of decomposition. As decomposition proceeded further, the cytoplasmic components were digested by bacteria, and the amount of SCD which does not comprise the cytoplasmic component increased, as shown in FIG. 1E. The bacteria used in the present example exhibit powerful activity for decomposing alginate and other many polysaccharides, and degraded the alginate present as an intercellular substance in the algal tissue to thereby allowing dispersion of the algal cells. The SCD diameter is about 10 μm, depending upon algal cell size. In the degrading process shown in FIG. 2, particles having a diameter of 5–15 μm increased at an early stage, but the peak of diameter distribution moved to smaller sizes as degradation proceeded further. As shown in FIG. 3, a high viable count was maintained during the culture. SCD prepared according to this example satisfied many of the requirements for an excellent nutrient feed, such as having degraded cellular structural components, forming a good suspension, having good floating properties and a dense coating of bacterial cells.

The SCD particles made above were fed to short-necked clam larvae to examine its suitability as a primary feed. Seven day old D-shaped larvae were put into a 300 ml glass beaker containing 100 ml of natural seawater, resulting in a final concentration of 10 bodies/ml. A suspension of SCD (0.4 ml) stained with neutral red on culture-day 3, was added thereto. The feed water at this point contained $2.8 \times 10^7$ CFU/ml of AR06 cells. After leaving the mixture with slight aeration overnight, the larvae were collected and microscopic observation was carried out. The results, shown in FIG. 4, indicate that the SCD was positively incorporated into the digestive organs of the short-necked clams. Many of the short-necked clams which preyed on the SCD retained their locomotive capability, which suggested that the SCD can be used for feed.

Example 2

Fronds of *Ulva pertusa* belonging to the class Chlorophyceae were washed with seawater, freeze-fried, pulverized and sieved to yield an algal powder having a diameter of less than 44 μm and an average diameter of 21 μm. Bacteria of the AR06 strain were inoculated and cultured under the same conditions as in example 1.

Bacterial attachment and proliferation on the surface of the algae was observed within 24 hours, as in the above example, and bacterial cells significantly attached to the surface until day 3, as shown in FIG. 5A. By more precise observation, it was found that algal cell walls made of cellulose were partially broken by bacterial degradation. By slightly shaking the culture, cytoplasm was released from the cells whose cell walls were broken, as shown in FIG. 5B. Within several days from initiation of the culture, cast-off shells which released SCD were obtained, as shown in FIG. 5C, as well as a large amount of protoplasmic SCD particles to whose surface bacterial cells were attached, as shown in FIGS. 5D–5F. As shown in FIG. 6, the diameter of the SCD was about 2–10 μm, which was almost the same as that obtained in Example 1. The diameter decreased as decomposition proceeded. During the culture, a high viable count of bacteria was maintained, as shown in FIG. 7.

SCD produced according to this example completely lost the hard cell walls present in the original algae and satisfied many of the requirements suitable for feed, such as forming a good suspension, having good floating properties and having attached bacterial cells. Stained SCD was injected into short-necked claims larvae (*Ruditapes philippinarum*) as described above, and was found to be incorporated into their digestive organs as shown in FIG. 8. Many of the short-necked clams which preyed on the SCD retained their locomotive capability, which suggested that the SCD can be used for feed.

Example 3

Damp-dried Laminaria frond power (0.5 g, diameter<44 μm) was suspended in each of four Erlenmeyer flasks containing 40 ml of 90% sea water and sterilized by an autoclave. These were cultured at 20° C. as follows: (a) no inoculation, shaking culture; (b) inoculation with the AR06 strain, shaking culture; (c) no inoculation, stirring culture, (d) inoculation with the AR06 strain, stirring culture. Shaking was carried out at 120 rpm and stirring was carried out at about 130 rpm (IUCHI Magnetic stirrer HS-360, stirring rate division 1). The number of SCD particles (2–10 μm) produced was determined using a Coulter multisizer. As shown in FIG. 9, the efficiency of producing SDC was improved by stirring and shaking.

Example 4

Damp-dried Laminaria frond power (5 g, diameter 105–177 μm) was suspended in each of two Erlenmeyer flasks and a magnetic bar of 40 mm size was placed in each flask, followed by sterilization in an autoclave. The AR06 strain was inoculated into one of the flasks and both were cultured at 20° C. for 17 hours by stirring at about 270–330 rpm (IUCHI Magnetic stirrer-HS-360, stirring rate division 3) to prepare the SCD suspension. The cultured mixture containing AR06 cells was preserved at 2° C. by keeping it stirred, resulting in Laminaria SCD feed. Non-SCD Laminaria feed prepared without bacterial inoculation also was preserved at 2° C. These two kinds of feeds were given to Artemia (2 ml/every 2 days) to examine their efficacy. In addition, a non-feeding control and a sample treated with digested Nannochloropsis (Nissin Science Co., Ltd., trade name: Marinealfa) also were investigated. Marinealfa was administered in an amount of 2 ml/2 days such that the amount of nitrogen administered with Marinealfa became up to 2.7 times greater than that in the Laminaria suspensions. The characteristics of each feed sample is shown in Table 2.

TABLE 2

Characteristics of the four feed samples

|  | no feed | Marinealfa | non-SCD Laminaria | SCD Laminaria |
|---|---|---|---|---|
| Amount of administration (once/every 2 days) Sample (ml) | 0 | 2 | 20 | 20 |
| Sterilized distilled water (ml) | 20 | 18 | 0 | 0 |
| Crude protein content (mg/once) | 0 | 38 | 14 | 14 |
| Particle allowable for predation (2–10 μm) number/once |  |  |  |  |
| Day 0 | <10³ | 1.4 × 10⁸ | 1.2 × 10⁶ | 2.0 × 10⁶ |
| Day 2 | NT* | NT* | NT* | NT* |
| Day 4 | NT* | NT* | 4.9 × 10⁵ | 6.4 × 10⁷ |
| Day 6 | NT* | NT* | 4.7 × 10⁵ | 8.2 × 10⁷ |

*Not tested

Bacteria free larvae prepared by sterilizing eggs of Artemia with sodium hypochlorite and hatching them for 48 hours were used in the experiment. 2.4 bodies/ml of the larvae in 2 liters of seawater were bred at 25° C. by aeration (4 l/min.). The feed efficacy was evaluated by determining viable counts (n–5) and body length (n=20) as time passed. Artemia which just hatched can not prey on particles of a size 20 μm or more. However, when Laminaria SCD having an average diameter of 6 μm was administered to Artemia, the SCD was incorporated into their digestive organs, as shown in FIG. 10. As seen in FIGS. 11A and B, both the viable counts and growth of the Artemia in SCD-Laminaria administered regions were higher than that in non-SCD (no bacterial inoculation) Laminaria and at the same level as in the region administered with Marinealfa, which is thought to be one of the best feeds for Artemia.

Example 5

Damp-dried Laminaria fronds (0.5 g, diameter<55 μm) were suspended in each of 8 Erlenmeyer flasks containing 50 ml of 90% seawater, and a 30 mm magnetic bar was placed therein and sterilized in an autoclave. Eight flasks were divided into 4 groups consisting of two flasks each and cultured by stirring (with an IUCHI Magnetic stirrer) at rate division of 0, 1 (about 130 rpm), 3 (about 330–400 rpm) or 5 (about 400–500 rpm). Diameters of SCD (2–10 μm) particles produced were measured using a Coulter multisizer. The results, shown in FIG. 12, show that bacteria free SCD particles could be prepared over a short time, such as 6–12 hours, using powerful stirring of 300 rpm or more.

Example 6

Damp-dried Laminaria fronds (5 g, diameter<44 μm) were suspended in an Erlenmeyer flask containing 500 ml of 90% concentration seawater and a 40 mm magnetic bar was placed therein, and sterilized at 120° C. in an autoclave for 5 minutes. These were cultured at 20° C. by stirring (with an IUCHI Magnetic stirrer HS-360) at a rate division of 3 (about 270–330 rpm) for 12 hours, and a portion (200 ml) of the cultured mixture was transferred into two 100 ml sterilized flasks. AR06 strain (2.4×10⁵) was inoculated into one of the two. They were cultured further at 20° C. by stirring at 330–400 rpm for 24 hours to yield feeds, which were kept at 5° C. The feed efficiency thereof was determined by administering these feeds into Artemia (10 ml/every 2 days). The number of feed particles available for predation in each test region is shown in Table 3.

TABLE 3

The number of feed particles in each test region

|  | no feed | bacteria free Laminaria SCD | AR06 Laminaria SCD |
|---|---|---|---|
| Dosage (once/every 2 days) |  |  |  |
| 1% w/v Laminaria suspension | 0 ml | 10 ml | 10 ml |
| Particles available for predation (2–10 μm) number/once |  |  |  |
| Day 0 | 0 | 3.8 × 10⁵ | 3.0 × 10⁵ |
| Day 2 | 0 | NT* | NT* |
| Day 4 | 0 | NT* | NT* |
| Day 6 | 0 | 4.0 × 10⁵ | 3.6 × 10⁵ |

*Not tested

Bacteria free larvae prepared by sterilizing eggs of Artemia with hypochloric acid and hatching them for 51 hours were used in the experiment. 3.9 bodies/ml of the larvae in 1 liter of seawater were bred at 25° C. by aeration. The feed efficacy was evaluated by determining viable counts (n=5) and body length (n=20) as time passed. Each test region has n=2 and the results were shown as means±standard error. The bacteria free detritus feed contained 3.8–4.0×10⁵ particles/10 ml having a diameter of 2–10 m suitable for Artemia's predation. Artemia preyed on Laminaria SCD particles with average 6 μm diameter regardless of bacterial attachment. As seen in FIGS. 13 A and B, high viable counts and growth were obtained. On day 8, the body length of Artemia in the bacteria free detritus region with the best results was 2.7 mm, which was very close to the growth rate obtained when Artemia was bred with digested Nannochloropsis under ideal conditions. Single cell Laminaria was found to show high feed efficacy equal to that of phytoplankton, which is conventionally used.

Example 7

Bacteria free Laminaria fronds prepared as in Example 5 were cultured at stirring rate division of 3 for 6 hours to yield physically prepared SCD. As one example of bacteria which could not make SCD, but had attachment capability, $10^8$ CFU of Alteromonas sp. T001 strain (deposited at National Research Institute of Fisheries Science, Fishery Agency, Ministry of Agriculture, Forestry and Fisheries) was inoculated therein, and cultured by shaking at 20° C. for 40 hours, followed by microscopic observation. It was observed that SCD having T001 strain bacteria attached was produced as shown FIG. 13.

What is claimed is:

1. A method for preparing algal detritus comprising contacting with algae, marine bacteria which belongs to genus Pseudoalteromonas, said bacteria being capable of attaching to the algae and decomposing structural components of said algae, thereby decomposing said algae into detritus comprising particles having substantially uniform diameters.

2. The method for preparing algal detritus according to claim 1 wherein said algae is from the class Phaeophyceae and is decomposed by said bacteria into single cells.

3. The method for preparing algal detritus according to claim 1 wherein said algae is from the class Chlorophyceae and its cell wall is degraded by said bacteria to form the detritus.

4. The method for preparing algal detritus according to claim 1 wherein said marine bacteria is *Pseudoalteromonas espejiana*.

5. The method for preparing algal detritus according claim 1 wherein said marine bacterium is Pseudoalteromonas AR06 strain (FERM BP-5024).

6. The method for preparing algal detritus according to claim 1 comprising the additional step of applying mechanical stirring during said contacting step.

7. The method for preparing algal detritus according to claim 1 wherein said particle diameter is about 2–10 μm.

8. A method for preparing bacteria-coated algal detritus comprising contacting with detritus obtained by the method according to claim 1 bacteria capable of attaching to said detritus, thereby forming detritus particles having bacteria on the surface thereof.

9. The method of claim 1 wherein said detritus comprises substantially single algae cells.

10. The method of claim 9 wherein cell walls of said single cells have been substantially removed by the action of said bacteria.

11. The method of claim 1 wherein said structural components comprise cell wall polysaccharides, intercellular polysaccharides and proteins.

* * * * *